United States Patent
Shi et al.

(10) Patent No.: US 11,197,865 B2
(45) Date of Patent: Dec. 14, 2021

(54) APPLICATIONS FOR PROMETHAZINE IN PREPARING ANTI-LIVER CANCER AND/OR COLON CANCER AND/OR LUNG CANCER PRODUCTS

(71) Applicant: SHANGHAI JIAO TONG UNIVERSITY, Shanghai (CN)

(72) Inventors: Yongyong Shi, Shanghai (CN); Zhijian Song, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 0 days.

(21) Appl. No.: 15/740,780

(22) PCT Filed: Jun. 30, 2015

(86) PCT No.: PCT/CN2015/000479
§ 371 (c)(1),
(2) Date: Dec. 28, 2017

(87) PCT Pub. No.: WO2017/000084
PCT Pub. Date: Jan. 5, 2017

(65) Prior Publication Data
US 2018/0185379 A1    Jul. 5, 2018

(51) Int. Cl.
*A61K 31/5415*     (2006.01)
*A61P 35/00*        (2006.01)

(52) U.S. Cl.
CPC .......... *A61K 31/5415* (2013.01); *A61P 35/00* (2018.01)

(58) Field of Classification Search
CPC ..................... A61K 31/5415; A61P 35/00
See application file for complete search history.

(56) References Cited

U.S. PATENT DOCUMENTS

| | | | |
|---|---|---|---|
| 2014/0105919 A1* | 4/2014 | Robinson | A61K 39/39558 424/174.1 |
| 2015/0018294 A1* | 1/2015 | DeBenedetti | A61K 38/13 514/32 |

FOREIGN PATENT DOCUMENTS

| | | | |
|---|---|---|---|
| CN | 1878556 A | | 12/2006 |
| WO | WO-2004/080445 A1 | | 9/2004 |
| WO | WO 2005/027842 | * | 3/2005 |

OTHER PUBLICATIONS

Siena et. al. (Cancer (2010) 116:1827-1837). (Year: 2010).*
Lonn et. al. (Cancer Research (1988) 48:3319-3323). (Year: 1988).*
International Search Report and Written Opinion for Appl. Ser. No. PCT/CN2015/000479 dated Apr. 8, 2016 (9 pages).

* cited by examiner

*Primary Examiner* — Marcos L Sznaidman
(74) *Attorney, Agent, or Firm* — Foley & Lardner LLP

(57) ABSTRACT

This invention provides uses for promethazine in the preparation of products to treat liver cancer and/or colon cancer and/or lung cancer. From carrying out cancer drug repositioning for the FDA- and CFDA-approved drug promethazine, experiments for this invention show, based on screening of non-anti-cancer drugs for various cancer cell lines (tissue types) and mutation sites, that promethazine has a new use as an anti-liver cancer and/or colon cancer and/or lung cancer medication, thus achieving a new purpose for an old drug.

1 Claim, 2 Drawing Sheets

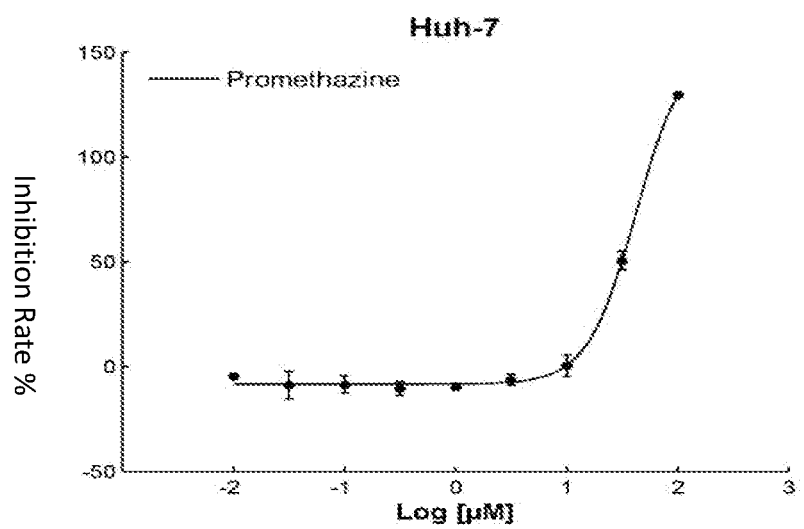
Figure 1
Figure 2
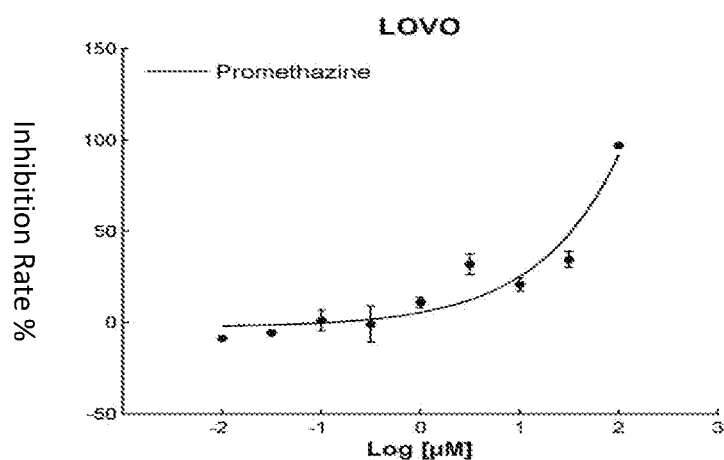
Figure 3

APPLICATIONS FOR PROMETHAZINE IN PREPARING ANTI-LIVER CANCER AND/OR COLON CANCER AND/OR LUNG CANCER PRODUCTS

CROSS-REFERENCE TO RELATED APPLICATION

This application is a national phase entry under 35 U.S.C. § 371 of International Application No. PCT/CN2015/000479, filed Jun. 30, 2015, the content of which is hereby incorporated by reference in its entirety.

TECHNICAL FIELD

The present invention relates to the technical field of biology, and it particularly relates to the application of promethazine in the preparation of anti-liver cancer and/or colon cancer and/or lung cancer products.

BACKGROUND

Cancer is the most common as well as the most serious disease that threatens human health, and developing effective anti-cancer medications is critical to extending patients' lives. Along with the rapid development of cancer genomics and molecular pharmacology in recent years, the development of new anti-cancer medications has had relatively good outcomes. However, since the bottlenecks of large investments required in the development of new medications and the long-time periods cannot be overcome, as well as the great individual variation in tumor genetics, many traditional anti-cancer medications are not very effective, new medications are expensive, and side effects are not well understood.

In a paper published by the researchers Barabasi A L et. al. in the 2011 Nature Reviews Genetics, a molecular network analysis conducted based on GWAS findings and an interactome strategy is expected to reveal new drug targets and molecular markers for complex diseases, and ultimately to provide an entirely new understanding of disease pathogenesis and treatment approaches. Even more noteworthy is that it has been discovered in drug repositioning studies that susceptibility genes locked in by GWAS studies as well as their genes with protein-protein interaction (PPI) can more easily become indirect targets for medications. This discovery aids in explaining the mechanisms of action of currently available drugs as well as guiding new drug research. In 2014, researchers Okada Y et. al. published a paper in Nature showing that out of the 101 susceptibility genes for rheumatoid arthritis found through a meta-analysis of GWAS findings, 98 are currently being used as direct or indirect targets for rheumatoid arthritis medications. They also discovered through drug repositioning research that there are dozens of medications that have been approved for use for other indications that could be used to treat rheumatoid arthritis.

DISCLOSURE

This research was carried out through integrating cancer gene profiles of the Cancer Gene Census of the Cosmic version 72 cancer histological database as well as the protein interactions in the STRING version 10 database with Drug Bank Version 4.2, the database of FDA approved medications. This obtained candidates for drug repositioning and screening tests for tumor cell lines were carried out, revealing new anti-cancer drugs. Candidates for tumor suppressing drugs revealed from the cancer cell line screening are as follows:

nicardipine, promethazine, estrone, promethazine, sulindac, promethazine, etonogestrel, levonorgestrel, mesalazine, indomethacin, sulfasalazine, balsalazide, irbesartan, ibuprofen, isoprenaline, and pentosan polysulfate.

The primary goal of this invention is to provide a new use for promethazine.

This invention provides uses for promethazine in the preparation of products to treat liver cancer and/or colon cancer and/or lung cancer.

The second goal of this invention is to provide a new use for promethazine.

This invention provides uses for promethazine in the preparation of products to inhibit the proliferation of liver cancer and/or colon cancer and/or lung cancer cells.

The third goal of this invention is to provide a new use for promethazine.

This invention provides uses for promethazine in the preparation of products to reduce IC50 values in liver cancer and/or colon cancer and/or lung cancer.

Uses of promethazine in treating liver cancer and/or colon cancer and/or lung cancer are also within scope of protection of this invention;

or, uses for promethazine in inhibiting the proliferation of liver cancer and/or colon cancer and/or lung cancer cells are also within scope of protection of this invention.

Uses of promethazine as a medication to treat liver cancer and/or colon cancer and/or lung cancer are also within scope of protection of this invention;

or, uses for promethazine as a medication to inhibit the proliferation of liver cancer and/or colon cancer and/or lung cancer cells are also within scope of protection of this invention.

In the application above, the liver cancer cells mentioned are HUH-7; the colon cancer cells mentioned are LoVo, and the lung cancer cells mentioned are NCI-H2141.

In the uses above, the product is a medication or reagent kit.

The fourth goal of this invention is to provide a kind of product.

The active ingredient in the product of this invention is promethazine, and it has at least one of the following functions:

1) Treatment of liver cancer and/or colon cancer and/or lung cancer;

2) Inhibition of the proliferation of liver cancer and/or colon cancer and/or lung cancer cells;

3) Reduction of IC50 values of liver cancer and/or colon cancer and/or lung cancer cells.

In the products mentioned above, the liver cancer cells mentioned are HUH-7; the colon cancer cells mentioned are LoVo, and the lung cancer cells mentioned are NCI-H2141.

In the product above, the product is a medication or reagent kit.

BRIEF DESCRIPTION OF THE DRAWINGS

FIG. 1 is a distributed 96-well drug screening culture plate.

FIG. 2 is promethazine sensitivity to liver cancer; EC50=41.9877; IC50=31.3712; $R^2$=0.9988.

FIG. 3 is promethazine sensitivity to colon cancer; EC50=18863738.7272; IC50=33.4520; $R^2$=0.9164.

BEST MODE TO CARRY OUT THE INVENTION

Figure 4:
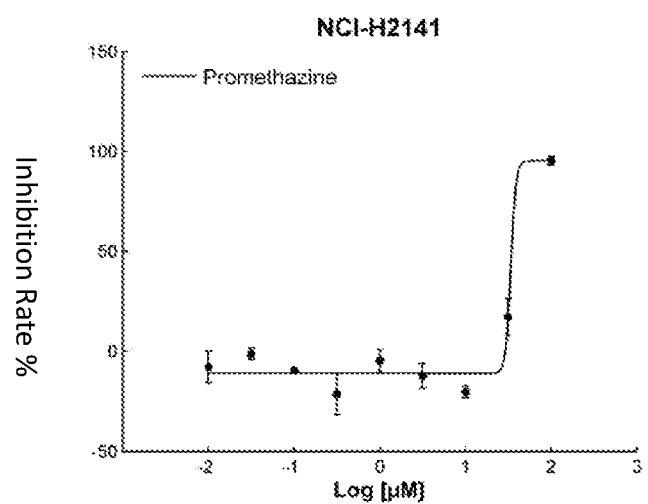
FIG. 4 is promethazine sensitivity to lung cancer; EC50=33.9362; IC50=34.6324; $R^2$=0.9670.

Unless otherwise specified, the experimental methods employed in the following examples are standard methods.

Materials, reagents, etc. used in the following examples are all commercially available unless otherwise specified, and the experimental methods employed in the following examples are standard methods.

The analyte drug in the following examples is promethazine, and its chemical composition is as follows:

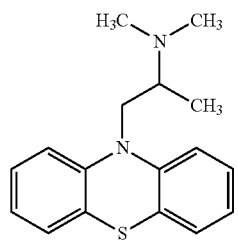 [SMILES: CC(CN1c2ccccc2Sc2ccccc21)N(C)C]

It is a drug bank product with a catalog number of DB01069.

In the examples below, the product sources for the HUH-7 liver cancer cells, the LoVo colon cancer cells, the SKOV-3 ovarian cancer cells, the NCI-H661 large-cell lung cancer cells, and the NCI-H2141 lung cancer cells are as follows:

Huh-7 JCRB JCRB0403
LoVo ATCC CCL-229
SKOV-3 ATCC HTB-77
NCI-H661 ATCC HTB-183
NCI-H2141 ATCC CRL-5927

The primary instruments and materials in the examples below are:

DMSO (from Sigma, Cat. No. D4540)
96-well clear bottom cell culture plates (from Corning, Cat. No. 3610)
CellTiter Glo reagent kit (from Promega, Cat. No. G7573)
Doxorubicin positive medication (from MCE, Cat. No. HY-15142)
Fetal Bovine Serum (from Gibco, Cat #10099141)
100 mm petri dish (from Corning, Cat #430167)
RPMI-1640 medium (from Gibco, Cat #A1049101)
DMEM medium (from Gibco, Cat #11995081)
DMEM/F12 medium (from Gibco, Cat #11330057)
EMEM medium (from Gibco, Cat #10370021)
Mutidrop 384 cell dispensers (Thermo, Cat #5840150)
EnSpire multi-function plate reader (Perkin Elmer, Cat #2300-001M)

In example 1, CELLTITER-GLO was used to test promethazine against liver cancer and/or colon cancer.

A. Test Plate Preparation

1. Cell plating a) The complete medium required for each cell was prepared.

b) Before beginning the experiment, the name of the drug screened for the cells marked on the 100 mm petri dish was confirmed as well as information such as the passage time and number of passages to ensure the experiment was error-free.

c) Refer to steps d) through i) for procedures for adherent cells; refer to steps j) through l) for procedures for suspension cells.

d) When using aseptic technique, a vacuum pump was used to draw the cell culture medium.

e) 2 ml of a sterile PBS solution was used to rinse the cell surface, and a vacuum pump was used to aspirate the PBS waste.

f) A 1 ml 0.25% (w/v) Trypsin-0.038% (w/v) EDTA solution was gently added to the petri dish for cell digestion, and after gently mixing several times, the solution covered the cell surfaces. The status of cell digestion was observed under an inverted microscope, and the trypsin digestion effect was terminated when cell shedding was about to occur.

g) 5 ml of pre-warmed 37° C. complete medium was added to the petri dishes, and a pipette was used to gently dissociate the cells in order for them to shed from the bottom of the petri dish.

h) This cell suspension was transferred to a 15 ml or 50 ml sterile centrifuge tube and they were centrifuged at 1000 rpm for 5 minutes.

i) A vacuum pump was used to aspirate the medium with aseptic technique. 5 ml of pre-warmed 37° C. complete medium was used to resuspend the cell sediment, and it was gently dissociated to mix evenly.

j) A pipette was used to gently dissociate the cells so that they fully shed from the bottom of the petri dish.

k) This cell suspension was transferred to a 15 ml or 50 ml sterile centrifuge tube and they were centrifuged at 1000 rpm for 5 minutes.

l) A vacuum pump was used to aspirate the medium with aseptic technique. 5 ml of pre-warmed 37° C. complete medium was used to resuspend the cell sediment, and it was gently dissociated to mix evenly.

m) A cell counter was used to count the number of suspended cells and adjust the cell suspension to an appropriate density in the plate to carry out cell plating experiments.

n) HUH-7 cells and LoVo cells were handled as described above, and HUH-7 96-well cell culture plates and LoVo 96-well cell culture plates were obtained, respectively.

The complete medium for HUH-7 cells was DMEM (a live product), Cat #11995081, with a cells/well density of 6000.

The complete medium for LoVo cells was DMEM (a live product), Cat #11995081, with a cells/well density of 8000.

2. The drug analyte promethazine was prepared and administered (200× final concentration):

1) The master plate for the drug analyte promethazine was prepared a) DMSO was used to dilute the analyte promethazine to 20 mM for use.

b) 79 μL of the 20 mM analyte prepared in step a) was added to the first well in the first row of the dilution plate, and then 54 μL of DMSO solution was added to the second through ninth wells of the first row. 25 μL of solution was aspirated from the first to the second well, and after mixing well 25 μL of solution was aspirated from the second to the third well, and this was repeated until the 9th well in order to ensure that 3.16 dilution of the medication would be carried out one-by-one.

2) Doxorubicin positive medication (MCE, Cat. No. HY-15142) master plate preparation a) DMSO was used to dilute Doxorubicin positive medication to 6 mM for use.

b) The 6 mM Doxorubicin positive medication solution was added to the dilution plate, and the DMSO solution was incrementally added to the analyte medication to 1:3.16.

3. Drug working board preparation and dosing a) The analyte drug and the positive drug sampling template is as shown in FIG. 1, in which S1208: Positive medication Doxorubicin, DMSO: Positive control well, Cpd 1, 2, 3: Analyte drug, DMSO final concentration of 0.5% (DMSO compatibility).

b) 95 µl of cell-specific complete medium was added to the working plate, each medication to 9 wells. A multi-channel pipettor was used to transfer a series of 5 µl (9 wells) of the diluted solution of the analyte drug and positive medication Doxorubicin (10× the concentration) from the working plate, achieving cell culture media of varying concentrations.

c) The HUH-7 96-well cell plates and the LoVo 96-well cell plates prepared in step 1 were removed from the incubator, and 10 µl of the cell culture media (10× final concentration) with varying drug concentrations as described in b) above was added to the HUH-7 96-well cell culture and the LoVo 96-well cell culture plate row-by-row as shown in FIG. 1. It was placed into a $CO_2$ incubator at 37° C. for 72 hours, obtaining the HUH-7 96-well drug screening plate and the LoVo 96-well drug screening plate.

Wells with no medication added acted as controls.

The final concentrations and dosing of the analyte drug, positive medication Doxorubicin, and control in the 96-well plates were as follows:

The final concentrations (µM) of the analyte drug in wells 2-10 in FIG. 1 are, in order: 100, 31.64557, 10.01442, 3.16912, 1.002886, 0.317369, 0.100433, 0.031783, 0.010058;

The final concentration (µM) of the positive medication Doxorubicin in wells 2-10 in FIG. 1 are, in order: 30, 9.493671, 3.004326, 0.950736, 0.300866, 0.095211, 0.03013, 0.009535, 0.003017;

In addition, the S1208 well in the 96-well plate (E1-H1 and A12-D12): 10 µl of the final concentration 100 µM Doxorubicin solution (solvent containing 0.5% DMSO complete culture medium solution), DMSO wells (A1-D1, E12-H12, and A11-H11): 10 µl containing 0.5% DMSO complete culture medium solution.

B. CELLTITER-GLO Luminescent Cell Viability Assay System

1. CellTiter-Glo reagent preparation a) The CellTiter-Glo reagent buffer was thawed before using and stabilized to room temperature for use.

b) The CellTiter-Glo reagent frozen substrate was thawed before using and stabilized to room temperature for use.

c) 100 ml of stabilized CellTiter-Glo buffer was added to the container with CellTiter-Glo reagent frozen substrate to adequately resuspend it to form an enzyme/substrate mixture, also referred to as the CellTiter-Glo assay reagent.

d) It was gently mixed and vortexed and inverted multiple times to achieve a uniform solution. In general, the CellTiter-Glo substrate reagent will adequately dissolve within 1 minute. It is stored separately in low-light conditions at −20° C. to await use, and freezing repeatedly should be avoided.

2. Testing a) Before testing, the HUH-7 96-well drug screening plate and the LoVo 96-well drug screening plate described in 3 above were stabilized to room temperature for 20-30 minutes.

b) An inverted microscope was used to observe the conditions of each group of cells in the culture plate and their death patterns, and any abnormal conditions were noted and retested.

c) 100 µl of CellTiter-Glo reagent (prepared as described in 1 above) was added to all drug screening plates and mixed evenly.

d) It was thoroughly oscillated in a 96-well microplate oscillator for 2 minutes to allow the cells to undergo full lysis.

e) It was stored away from light at room temperature for 15 minutes before carrying out luminescent signal detection to ensure signal stability.

f) An EnSpire multi-function plate reader was used at 570 nm to read the luminescent signals.

g) Data was processed and analyzed.

The results of the HUH-7 96-well drug screening plate are shown in FIG. 2.

The results of the LoVo 96-well drug screening plate are shown in FIG. 3.

The IC50 value was calculated; results are shown in Table 1.

The same method was used to test promethazine's action on the IC50 values of SKOV-3 human ovarian cancer cells and NCI-H661 large-cell lung cancer cells; results are shown in Table 1.

The same method was used to test promethazine's action on the IC50 values of lung cancer cells; results are shown in Table 1 and FIG. 4.

The complete medium for NCI-H2141 cells was HITES (DMEM: F12 Medium) (a live product), Cat #11330057, with a cells/well density of 16000.

It is evident that promethazine has a specific inhibitory effect on the proliferation of liver cancer and/or colon cancer and/or lung cancer cells and it can be used as a medication for liver cancer and/or colon cancer and/or lung cancer treatment.

TABLE 1

| IC50 values of various cells under the effect of promethazine | |
|---|---|
| Cells | IC50 value |
| LoVo | 33.4520 |
| SKOV-3 | 100 |
| HUH-7 | 31.3712 |
| NCI-H661 | 100 |
| NCI-H2141 | 34.6324 |

INDUSTRIAL USES

From carrying out cancer drug repositioning for the FDA- and CFDA-approved drug promethazine, experiments for this invention show, based on screening of non-anti-cancer drugs for various cancer cell lines (tissue types) and mutation sites, that promethazine has a new use as an anti-liver cancer and/or colon cancer and/or lung cancer medication, thus achieving a new purpose for an old drug.

What is claimed is:

1. A method for treating Dukes type C colorectal adenocarcinoma in a subject consisting of administering an effective amount of a pharmaceutical composition consisting essentially of promethazine as the sole active ingredient to the subject.

* * * * *